(12) United States Patent
Guan et al.

(10) Patent No.: US 10,352,794 B2
(45) Date of Patent: Jul. 16, 2019

(54) TURBINE BLADE FATIGUE LIFE ANALYSIS USING NON-CONTACT MEASUREMENT AND DYNAMICAL RESPONSE RECONSTRUCTION TECHNIQUES

(71) Applicant: Siemens Energy, Inc., Orlando, FL (US)

(72) Inventors: Xuefei Guan, Princeton, NJ (US); Jingdan Zhang, Plainsboro, NJ (US); Shaohua Kevin Zhou, Plainsboro, NJ (US); Nancy H. Ulerich, Longwood, FL (US); Nam Eung Kim, Jupiter, FL (US); Nikolai R. Tevs, Daytona Beach Shores, FL (US)

(73) Assignee: Siemens Energy, Inc., Orlando, FL (US)

( * ) Notice: Subject to any disclaimer, the term of this patent is extended or adjusted under 35 U.S.C. 154(b) by 1479 days.

(21) Appl. No.: 14/028,594

(22) Filed: Sep. 17, 2013

(65) Prior Publication Data
US 2014/0100798 A1    Apr. 10, 2014

Related U.S. Application Data

(60) Provisional application No. 61/710,179, filed on Oct. 5, 2012.

(51) Int. Cl.
*G01L 5/00*    (2006.01)
*G01M 5/00*    (2006.01)
(Continued)

(52) U.S. Cl.
CPC .............. *G01L 5/00* (2013.01); *G01M 5/0016* (2013.01); *G01M 5/0041* (2013.01);
(Continued)

(58) Field of Classification Search
CPC ....... G01L 5/00; G01M 5/0041; G01M 15/14; G01M 5/0016; G06F 19/00; G06F 17/40; G01N 3/56; G01D 21/00; G01H 17/00
See application file for complete search history.

(56) References Cited

U.S. PATENT DOCUMENTS

| | | | | |
|---|---|---|---|---|
| 5,327,358 A | * | 7/1994 | Stubbs | G01H 17/00 |
| | | | | 702/36 |
| 6,041,132 A | * | 3/2000 | Isaacs | G01N 23/046 |
| | | | | 378/21 |

(Continued)

FOREIGN PATENT DOCUMENTS

| CN | 1038696 A | 1/1990 |
|---|---|---|
| CN | 1517691 A | 8/2004 |

(Continued)

OTHER PUBLICATIONS

Lin, Application of AE techniques for the detection of wind turbine using Hilbert-Huang transform, 2010, IEEE, pp. 1-7.*

(Continued)

Primary Examiner — Sujoy K Kundu
Assistant Examiner — Lisa E Peters

(57) ABSTRACT

A method dynamically reconstructing a stress and strain field of a turbine blade includes providing a set of response measurements from at least one location on a turbine blade, band-pass filtering the set of response measurements based on an upper frequency limit and a lower frequency limit, determining an upper envelope and a lower envelope of the set of response measurements from local minima and local maxima of the set of response measurements, calculating a candidate intrinsic mode function (IMF) from the upper envelope and the lower envelope of the set of response measurements, providing an N×N mode shape matrix for the turbine blade, where N is the number of degrees of freedom of the turbine blade, when the candidate IMF is an actual (Continued)

IMF, and calculating a response for another location on the turbine blade from the actual IMF and mode shapes in the mode shape matrix.

23 Claims, 7 Drawing Sheets

(51) Int. Cl.
*G01M 15/14* (2006.01)
*G06F 19/00* (2018.01)
*G01N 3/56* (2006.01)
*G01D 21/00* (2006.01)
*G01H 17/00* (2006.01)
*G06F 17/40* (2006.01)

(52) U.S. Cl.
CPC .......... *G01M 15/14* (2013.01); *G01D 21/00* (2013.01); *G01H 17/00* (2013.01); *G01N 3/56* (2013.01); *G06F 17/40* (2013.01); *G06F 19/00* (2013.01)

(56) References Cited

U.S. PATENT DOCUMENTS

| | | | |
|---|---|---|---|
| 7,555,951 B2* | 7/2009 | Shadman | G01H 1/14 73/579 |
| 2003/0167099 A1* | 9/2003 | Kesavadas | B29C 64/386 700/119 |
| 2005/0278127 A1* | 12/2005 | Griffin | G01H 1/006 702/56 |
| 2007/0272018 A1 | 11/2007 | Chougule | |
| 2008/0124480 A1* | 5/2008 | Shen | C23C 4/08 427/456 |
| 2009/0082976 A1* | 3/2009 | Anuzis | G01H 1/006 702/35 |
| 2009/0198474 A1* | 8/2009 | Fritz | G01M 15/06 702/183 |
| 2012/0031193 A1* | 2/2012 | Adams | G01L 25/00 73/804 |
| 2012/0051911 A1* | 3/2012 | Baik | G01M 5/0016 416/61 |
| 2012/0271824 A1* | 10/2012 | Goldfine | G01N 27/90 707/736 |
| 2013/0268214 A1* | 10/2013 | Guan | G01N 29/4472 702/34 |
| 2014/0100798 A1* | 4/2014 | Guan | G01M 5/0041 702/42 |

FOREIGN PATENT DOCUMENTS

| | | |
|---|---|---|
| CN | 101688824 A | 3/2010 |
| CN | 102156040 A | 8/2011 |
| CN | 102393331 A | 3/2012 |
| CN | 102607831 A | 7/2012 |
| CN | 102436515 A | 5/2015 |
| EP | 0327865 A2 | 8/1989 |
| JP | S54147890 A | 11/1979 |
| JP | 2008134182 A | 6/2008 |
| WO | WO 2013/152085 A1 * | 10/2013 |

OTHER PUBLICATIONS

Ghasemi, Damage Detection Method by Using Inverse Solution of Equations of Motion in Frequency Doamin, Sep. 24-28, 2012, 15 WCE, pp. 1-10.*
Huang, A Review on Hilbert-Huang Transform: Method and its Applications to Geophysical Studies, 2008, American Geophysical Union, pp. 1-23.*
Rao, Mechanical Vibrations, Fifth Edition, University of Miami, 2011, pp. 467-653.*
Koyamada et al, Volume Visualization of 3D FEM Results, 1991, IBM. Res. Develop. vol. 33 No. 1/2 Jan./Mar. 1991, pp. 12-25 (Year: 1991).*
Norden E. Huang, et al., "The Empirical Mode Decomposition and the Hilbert Spectrum for Non-Linear and Non-Stationary Time Series Analysis," pp. 903-995, Proc. R. Soc. Lond. A (1998), 454.
Jingjin He, et al., "Structural Response Reconstruction Based on Empirical Mode Decomposition in Time Doman," Mechanical Systems and Signal Processing 28 (2012) 348-366.
PCT International Search Report mailed Mar. 11, 2014 corresponding to PCT International Application No. PCT/US2013/063377 filed Oct. 4, 2013 (12 pages).
"Analytical Formulation of the Jacobian Matrix for Non-Linear Calculation of the Forced Response of Turbine Blade Assemblies with Wedge Friction Dampers" vol. 41, No. 10, Dec. 1, 2006; pp. 1118-1127, XP028070068.
Chih-Chen Chang et al: "Multi-component signal decomposition techniques for structural health monitoring"; Proceedings of SPIE; pp. 873-880; May 17, 2005; SPIEDigitallibrary.org/conference-proceedings-of-spie.
Report of Examination dated Jun. 19, 2017; Chinese Application No. 201380063801.6; 21 pages.
Deyuan Li et al.: "Load Spectrum and Fatigue Life Analysis of the Blade of Horizontal Axis Wind Turbine"; pp. 118-123; Engineering Mechanics; No. 6; vol. 21; / Dec. 12, 2004.

* cited by examiner ated by block 11, and (2) non-synchronous vibrations, represented by block 12. Synchronous vibrations are excited by drivers which are stationary to an engine case and typically located in the flow field. The frequencies of these vibrations are locked in phase with the engine speed. Synchronous vibrations are analyzed by least squares based modeling techniques, such as LSMF (least squares model fit) and SDOF (single degree of freedom) analysis. Non-synchronous vibrations are excited by drivers that are typically non-stationary and are thus not tied to the engine speed. Energy that enters the system causes rotor bladders to vibrate along their natural frequency modes. Non-synchronous vibrations can use FFT based analysis techniques, such as TRAV (traveling wave) and IND (individual blade) techniques, but the frequencies are typically aliased. The output of these analyses combined with a finite element model (FEM) 13, yields mode shapes 14, which are represented as an N×N matrix, where N is the number of degrees of freedom. The mode shapes, which can be derived from the FEM, can be used to calculate stress-to-deflection ratio curves 15, which can be used to calculate the stress at the measurement locations 16 and to calculate S-N curves 17 for the high-cycle fatigue (HCF) life prediction.

TURBINE BLADE FATIGUE LIFE ANALYSIS USING NON-CONTACT MEASUREMENT AND DYNAMICAL RESPONSE RECONSTRUCTION TECHNIQUES

CROSS REFERENCE TO RELATED UNITED STATES APPLICATIONS

This application claims priority from "System And Method For Turbine Blade Fatigue Life Analysis Using Non-Contact Measurement And Dynamical Response Reconstruction Techniques", U.S. Provisional Application No. 61/710,179 of Guan, et al., filed Oct. 5, 2012, the contents of which are herein incorporated by reference in their entirety.

TECHNICAL FIELD

This application is directed to turbine blade fatigue life analysis using non-contact measurement and dynamical response reconstruction techniques.

DISCUSSION OF THE RELATED ART

Fatigue is the progressive and localized structural damage that occurs when a material is subjected to cyclic loading. Traditionally, most attention has focused on situations that require more than $10^4$ cycles to failure where stress is low and deformation is primarily elastic, known as high-cycle fatigue situations. In these situations, material performance is commonly characterized by an S-N curve, which graphs the magnitude of a cyclic stress (S) against the logarithmic scale of cycles to failure (N). S-N curves are derived from tests on samples of the material to be characterized where a regular sinusoidal stress is applied by a testing machine which also counts the number of cycles to failure.

Turbine blades are key components of turbines. Blade failure can be costly due to the fact that the failure of one blade can damage other blades and cause the downtime of an entire system; therefore, improving blade durability can help reduce life-cycle cost of a turbine system. The fatigue life of a turbine blade is an important quantity for assessing durability. In the turbine blade fatigue life analysis, accurate and reliable estimate of the stress the stress and strain fields is significant for fatigue life prediction using S-N curve- or da/dN-based methods, which characterize a crack length growth as a function of cycles. Both the design phase and the operation phase of a turbine require evaluations of the fatigue life of the turbine blades. In the design phase, finite element models are used to perform numerical experiments under different operating conditions to locate the hot spots, that is, locations subject to high stresses, based on model stresses results. In the operational phase, measurements are made using contact or noncontact sensors to indirectly evaluate the stress fields for those hot spots. The traditional analysis might have a potential limitation of that the monitoring system can only monitor a few surface locations. Traditional contact or non-contact measurement may have spatially sparse measurements of the entire blade and only those locations that have measurement data can be used for further analysis The workflow of a conventional turbine blade non-contact measurement and fatigue analysis system and method is illustrated in FIG. 1. Referring now to FIG. 1, tip-timing measurements are acquired at block 10. The probes used for these measurements provide one deflection measurement for every blade of revolution. The sample rate is low and is synchronized to the engine rotation. The arrival times of each blade are converted to deflections by knowing the rotational velocity and the radius at the measurement location. There are two general types of vibrations that can be analyzed: (1) synchronous vibrations, represented by block Conventional systems and methods have some drawbacks:

(1) The system and method can only measure a few points due to the hardware constraints. The stress or strain fields of the entire blade are difficult to infer.

(2) The stress and strain field analysis depends on the stress-to-deflection ratio which is not the physical dynamical responses of the stress and strain.

(3) The measurement location or sensor layout must be carefully designed to achieve an accurate estimate of the fatigue life. Since only a few locations can be measured and the locations must be optimized, this introduces a combinatorial optimization challenge for the sensor layout and finite element analysis.

(4) Visualization of the stress or strain fields of the entire blade can be challenging, particularly spatial locations below the blade surface. For example, visualizing a cross-section of the blade based on user selection is not available in a conventional system.

SUMMARY

Exemplary embodiments of the invention as described herein generally include systems and methods for reconstructing the stress and strain fields of an entire blade using sparse surface location measurement data. After the reconstruction, the fatigue life of an arbitrary spatial location of the blade geometry can be calculated for design optimization and condition-based maintenance.

According to an aspect of the invention, there is provided a method dynamically reconstructing a stress and strain field of a turbine blade, including providing a set of response measurements from at least one location on a turbine blade, band-pass filtering the set of response measurements based on an upper frequency limit and a lower frequency limit, determining an upper envelope and a lower envelope of the set of response measurements from local minima and local maxima of the set of response measurements, calculating a candidate intrinsic mode function (IMF) from the upper envelope and the lower envelope of the set of response measurements, providing an N×N mode shape matrix for the turbine blade, where N is the number of degrees of freedom of the turbine blade, when the candidate IMF is an actual IMF, and calculating a response for another location on the turbine blade from the actual IMF and mode shapes in the mode shape matrix.

According to a further aspect of the invention, the upper frequency limit and the lower frequency limit of the set of response measurements are determined by Fourier transforming the set of response measurements and identifying major frequency components by peak picking.

According to a further aspect of the invention, the at least one location on the turbine blade is a tip location.

According to a further aspect of the invention, the upper envelope and the lower envelope of the a set of response measurements are determined from cublic splines that connect the local minima and local maxima of the a set of response measurements.

According to a further aspect of the invention, calculating a candidate IMF from the upper envelope and the lower envelope of the set of response measurements includes calculating a mean envelope of the upper envelope and the lower envelope of the set of response measurements, and calculating the candidate IMF by subtracting the mean envelope from the set of response measurements.

According to a further aspect of the invention, if the candidate IMF is not an actual IMF, the steps of determining an upper envelope and a lower envelope and calculating a mean envelope of the upper envelope and the lower envelope are performed on the candidate IMF, and a new candidate IMF is calculated by subtracting the mean envelope of the previous candidate IMF from the previous candidate IMF.

According to a further aspect of the invention, the method includes repeating the steps of determining an upper envelope and a lower envelope of the set of response measurements and calculating a candidate intrinsic mode function (IMF) from the upper envelope and the lower envelope of the set of response measurements until no further IMFs can be calculated from the set of response measurements.

According to a further aspect of the invention, the N×N mode shape matrix is calculated by solving the eigensystem of $(M^{-1}K)$, where M is a matrix that represents a mass of a turbine blade and K is a matrix that represents a stiffness of the turbine blade.

According to a further aspect of the invention, calculating a response for another location on the turbine blade comprises calculating $$\delta_{iu} = \frac{\phi_{iu}}{\phi_{ie}} \delta_{ie},$$

where subscript e represents a degree of freedom (DOF) that can be measured, u represents a DOF that is inaccessible for measurements, and i represents an ith mode, $\varphi_{ik}$ represents the mode shape for the kth DOF under the ith mode, and $\delta_{ie}$ represents the ith IMF for the eth DOF.

According to a further aspect of the invention, the method includes calculating an S-N curve-based fatigue life estimation from the calculated responses.

According to another aspect of the invention, there is provided a method for dynamically reconstructing a stress and strain field of a turbine blade, including providing a set of response measurements from at least one location on a turbine blade, using empirical mode decomposition to determine intrinsic mode functions (IMFs) from set of response measurements, and calculating a response for another location on the turbine blade by calculating $$\delta_{iu} = \frac{\phi_{iu}}{\phi_{ie}} \delta_{ie},$$

where subscript e represents a degree of freedom (DOF) that can be measured, u represents a DOF that is inaccessible for measurements, and i represents an ith mode, $\varphi_{ik}$ represents a mode shape for the kth DOF under the ith mode, and $\delta_{ie}$ represents the ith IMF for the eth DOF, where the mode shape is a component of an N×N mode shape matrix calculated by solving the eigenvectors of $(M^{-1}K)$, where M is a matrix that represents a mass of a turbine blade and K is a matrix that represents a stiffness of the turbine blade.

According to a further aspect of the invention, using empirical mode decomposition to determine intrinsic mode functions (IMFs) includes determining an upper envelope and a lower envelope of the set of response measurements from local minima and local maxima of the set of response measurements, calculating a mean envelope of the upper envelope and the lower envelope of the set of response measurements, and calculating the candidate IMF by subtracting the mean envelope from the set of response measurements.

According to a further aspect of the invention, the method includes determining an upper frequency limit and a lower frequency limit of the set of response measurements by Fourier transforming the set of response measurements and identifying major frequency components by peak picking, and band-pass filtering the set of response measurements based on the upper frequency limit and the lower frequency limit, prior to using empirical mode decomposition to determine intrinsic mode functions (IMFs).

According to another aspect of the invention, there is provided a non-transitory program storage device readable by a computer, tangibly embodying a program of instructions executed by the computer to perform the method steps for dynamically reconstructing a stress and strain field of a turbine blade.

DETAILED DESCRIPTION OF EXEMPLARY EMBODIMENTS

Figure 1:
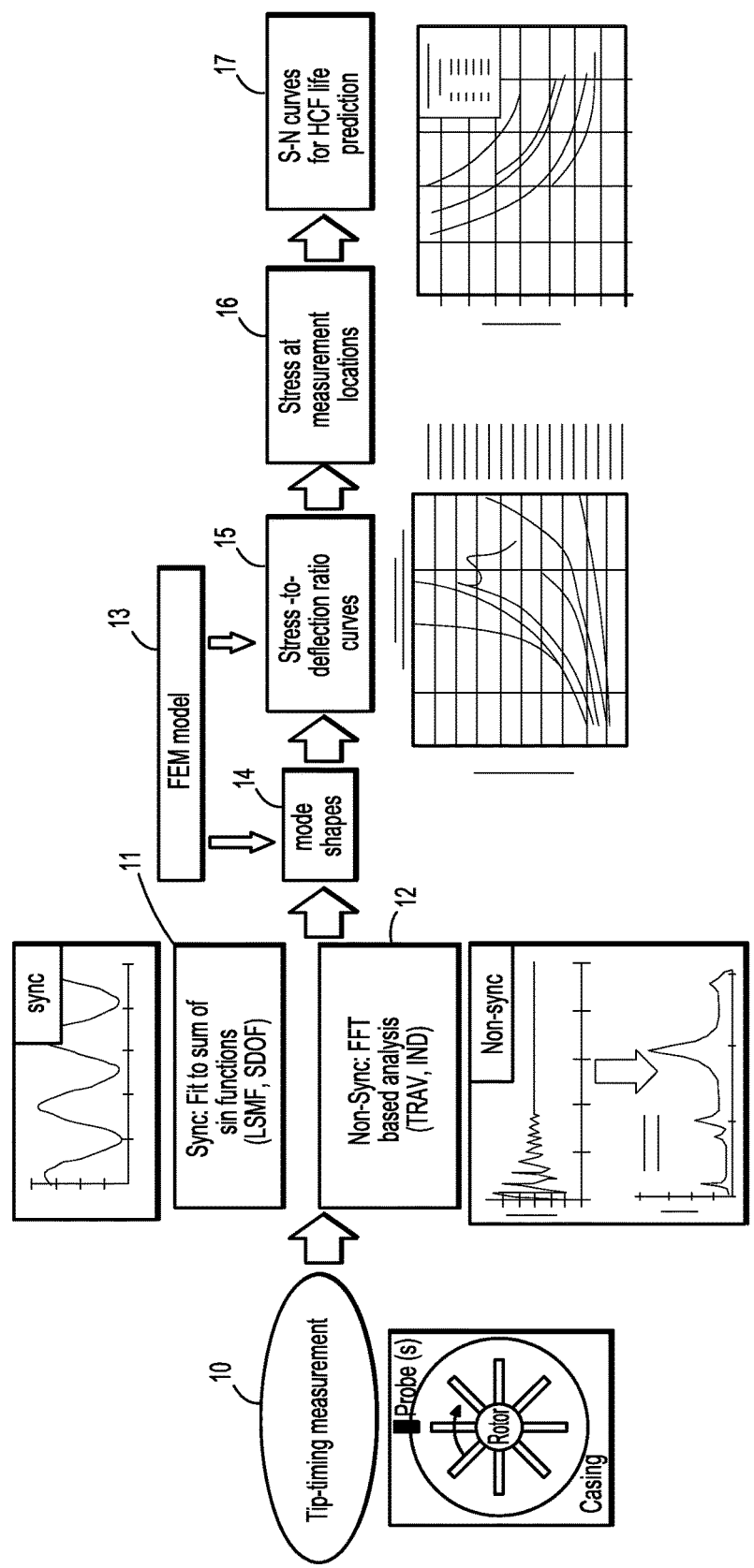
FIG. 1 illustrates a workflow of a conventional system and method, according to an embodiment of the disclosure.

Exemplary embodiments of the invention as described herein generally provide systems and methods for dynamical response reconstruction. While embodiments are susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

Figure 2:
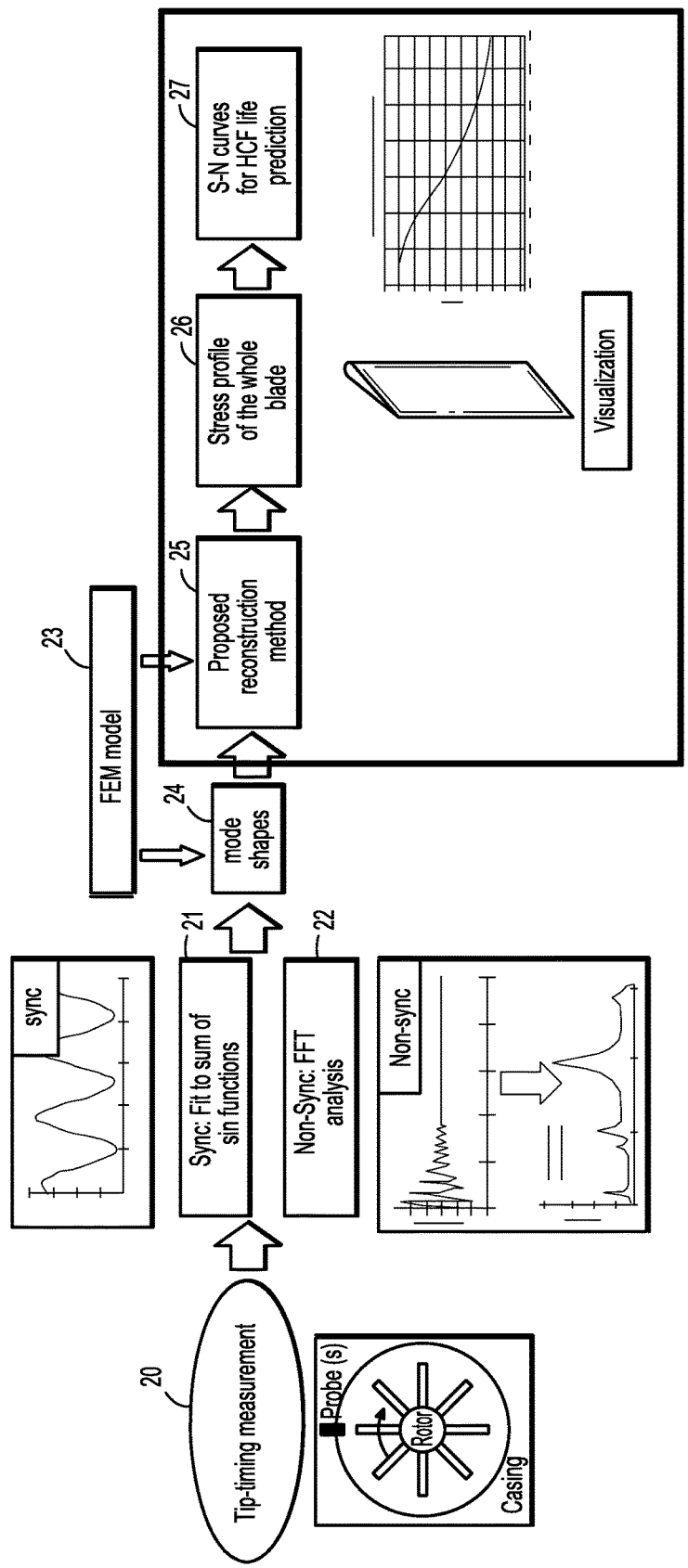
FIG. 2 illustrates a workflow a system and method according to an embodiment of the disclosure.

A system and method according to embodiments of the disclosure can address the drawbacks of conventional systems and methods by using dynamical response reconstruction methodologies. The basic idea is to reconstruct the stress and strain fields of the entire blade based on a finite element model, the measured responses and an empirical mode decomposition technique. A workflow of a system and method according to embodiments of the disclosure is illustrated in FIG. 2. Blocks 20 to 24 of FIG. 2 correspond to blocks 10 to 14 of FIG. 1, and thus will not be described further. At block 25, the mode shapes and the FE model are used with a reconstruction method according to an embodiment of the disclosure to calculate stresses for a whole turbine blade, based on the tip measurement. Details of reconstruction method according to an embodiment of the disclosure are provided below with reference to FIG. 3, described below. Once stresses have been calculated for the entire blade, a stress profile for the whole blade can be visualized at block 26, and S-N curves can be calculated for the high-cycle fatigue (HCF) life prediction at block 27.

A dynamical response reconstruction method according to an embodiment of the disclosure is based on a structural model and an empirical mode decomposition (EMD) technique with an intermittency criteria, and includes two steps. A first step is to decompose the measured signals into modal responses, known as intrinsic model functions (IMFs), using EMD with an intermittency criteria. The resulting IMFs are used in a second step to reconstruct the dynamic responses at critical locations which are sensor-inaccessible.

The idea of EMD is to break down a given signal into functions which form a complete and nearly orthogonal basis for the original signal. The resulting functions, which have a mean value of zero and only one extreme between zero crossings, known as IMFs, are sufficient to describe the underlying dynamics of the signal.

An intrinsic mode function (IMF) is a function that satisfies two conditions: (1) In the whole data set, the number of extrema and the number of zero crossings is either equal or differ at most by one; and (2) at any point, the mean value of an envelope defined by the local maxima and an envelope defined by the local minima is zero. With this definition, the IMF in each cycle, defined by the zero crossings, involves only one mode of oscillation, with no complex riding waves.

The sufficiency and completeness of the EMD method is ensured by the way the signal is decomposed. Using IMFs to represent the signal allows for time varying frequencies to be preserved, which is hidden in the Fourier or wavelet domains.

To filter IMFs out from a given signal, the EMD method employs a sifting process. To obtain IMFs corresponding to a system's modal responses, an intermittency frequency denoted by $\omega_{int}$ can be imposed on the sifting process to ensure that each of the IMFs contains only one frequency component. This idea, known as an intermittency criteria, is to remove all frequency components lower and larger than $\omega_{int}$ from an IMF, and this can be done during the sifting process using a band-pass filter.

Figure 3:
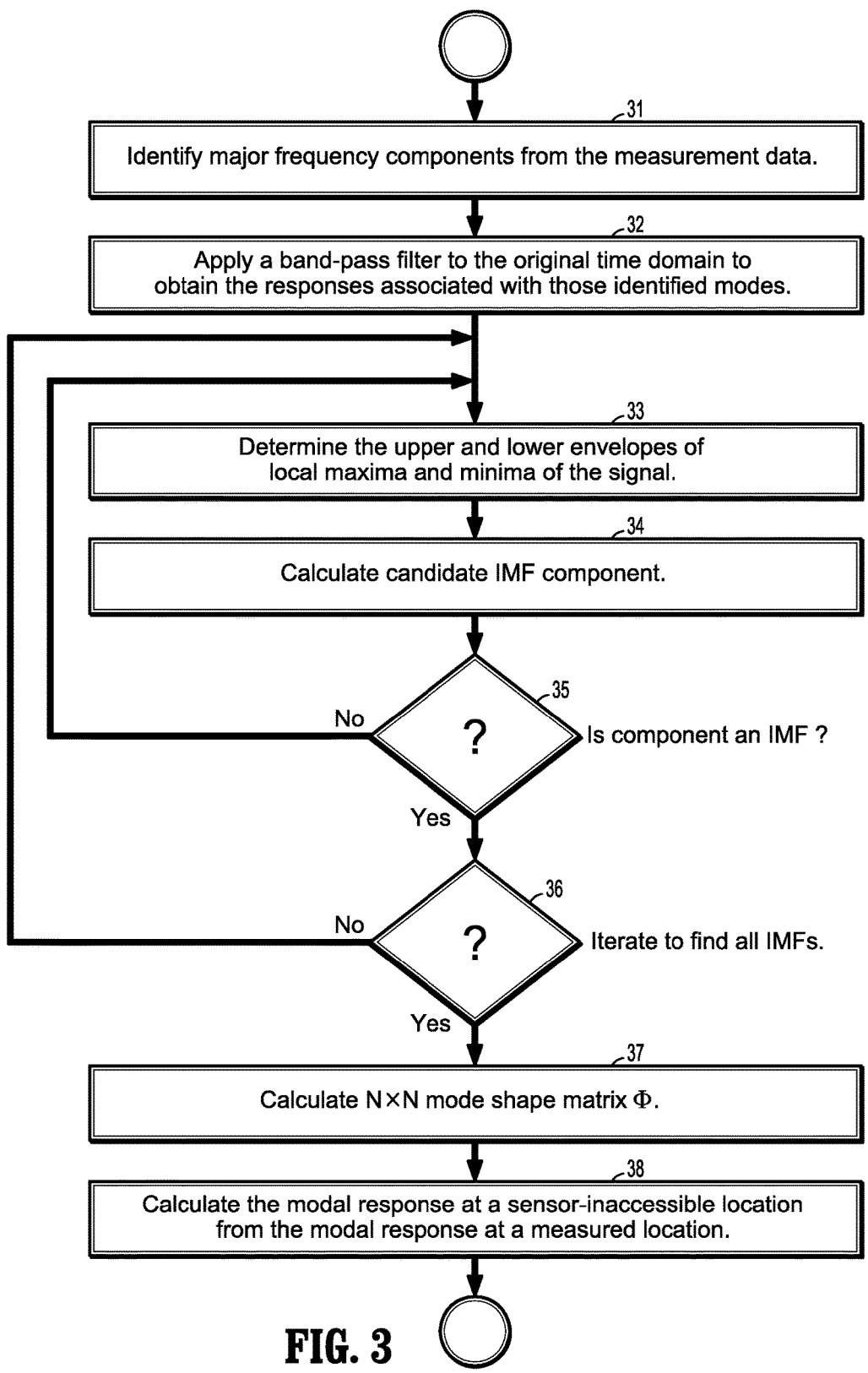
FIG. 3 is a flowchart of a dynamical response reconstruction method, according to an embodiment of the disclosure.

FIG. 3 is a flowchart of a dynamical response reconstruction method according to an embodiment of the disclosure for reconstructing dynamical responses at B using measurements at A, according to embodiments of the disclosure. For a time domain signal, denoted as y(t), a sifting process according to an embodiment of the invention is as follows Referring now to the figure, at step 31, major frequency components are identified from the measurement data using either a Fast Fourier Transform (FFT) or FEM computations. These are used to identify upper $\omega_{iH}$ and lower $\omega_{iL}$ limits for $\omega_{int}$: $\omega_{iL}<\omega_i<\omega_{iH}$. After the FFT, the major frequency components can be identified using a peak picking algorithm on the Fourier spectra. Next, band-pass filtering in the frequency range $\omega_{iL}<\omega_i<\omega_{iH}$ is applied to the original time domain data y(t) at step 32 to obtain the responses associated with those identified modes. Then, at step 33, the upper and lower envelopes are determined from the local maxima and minima of the signal. An exemplary, non-limiting technique for calculating the upper and lower envelopes uses a cubicspline interpolation to connect the local maxima and connect the local minima. Let $m_1$ denote the mean envelope of the upper and lower envelopes. A first candidate component is calculated as $h_1=y(t)-m_1$ at step 34, and it is determined at step 35 whether $h_1$ is an IMF. If not, the result of step 35 is NO, and steps 33 and 34 are repeated, this time using $h_1$ as the new signal, instead of y(t). Here, the new the mean envelope is denoted $m_{11}$, and the new candidate component is $h_{11}=h_1-m_{11}$, where $m_{1k}$ is the mean of the upper and lower envelopes of the kth iteration. Steps 33 and 34 are repeated from step 35 until the resulting $h_{1k}$ (i.e., $h_{1k}=h_{1(k-1)}-m_{1k}$) is an IMF. The first IMF component from the data may be denoted as $f_1(t)=h_{1k}$. It contains the shortest period component of the signal, and is the response under modal coordinates. If the present candidate component is an IMF, then the result of step 35 is YES and flow proceeds to step 36.

As described above, a dynamical response reconstruction process according to an embodiment of the disclosure separates the finest local mode from the data based only on the characteristic time scale. A sifting process according to an embodiment of the disclosure, however, has two effects: (a) to eliminate riding waves; and (b) to smooth uneven amplitudes. However, the second effect can obliterate physically meaningful amplitude fluctuations. To guarantee that the IMF components retain enough physical sense of both amplitude and frequency modulations, there should be a stopping criteria. This can be accomplished by limiting the size of the standard deviation, SD, computed from the two consecutive sifting results. Based on the SD for two Fourier spectra computed by shifting five out of 1024 points from the same data, an exemplary, non-limiting SD value can be set to between 0:2 and 0:3.

At Step 36, it is determined if more IMFs exist in the measurement data. If more IMFs exist (i.e., all IMFs are not found) the answer at Step 36 is NO and flow returns to Step 33. Otherwise, all IMFs are found, the answer at Step 36 is YES and the process proceeds to Step 37. Steps 33 to 35 above can be repeated from step 36 to obtain a second IMF $f_2(t)$ from the remainder signal $r_1(t)=y(t)-f_1(t)$. These steps can be repeated to obtain up to an nth IMF. A determination that all IMFs are found may be achieved by a sifting process according to an embodiment of the disclosure that can be stopped by any of the following criteria: either when the IMF component, $f_n$, or the remainder, $r_n$, becomes so small that it is less than a predetermined value, or when the remainder, $r_n$, becomes a monotonic function from which no further IMFs can be extracted. Even for data with zero mean, the final remainder can still be different from zero; for data with a trend, then the final remainder $r_n(t)=y(t)-\Sigma_i f_i(t)$ should be that trend.

By applying an EMD method with a sifting process according to an embodiment of the disclosure to the sensor measurement data, all required modal responses can be extracted without leaving the time domain. The original signal y(t) can be expressed as the summation of n IMFs and a remainder term, as shown in EQ. (1).

$$y(t) = \sum_{i=1}^{n} f_i(t) + r(t) \tag{1}$$

where $f_i(t)$ is the ith IMF and r(t) is the remainder. By repeating with different frequency ranges for different natural frequencies, all modal responses can be obtained. Using a sifting process with an intermittency criteria according to an embodiment of the disclosure, the original signal expression can be written as Eq. (2).

$$y(t) \approx \sum_{i=1}^{m} x_i(t) + \sum_{i=1}^{n-m} f_i(t) + r(t) \tag{2}$$

where $x_i(t)$ is a modal response (that is also an IMF) for the ith mode. Terms $f_i(t)$, i=1, . . . , n×m, are other IMFs but not modal responses.

These IMFs have several characteristics:

(1) Each IMF contains the intrinsic characteristics of the signal;

(2) Once an IMF is obtained, the next IMF will have a different frequency at the same time instant; and (3) The first IMF for each IMF series is considered to be the approximation of modal response.

The modal responses obtained above are then used to extrapolate the modal responses at the desired location for each of the identified modes using a transformation equation. The sensor measurements in the time domain have been decomposed into several IMFs using the EMD method with intermittency criteria. The dynamic responses at locations other than the sensor locations can be extrapolated using transformation equations. Those transformation equations can be derived from the finite element model of the target structure.

Referring again to FIG. 3, an extrapolation procedure according to an embodiment of the disclosure is as follows.

Consider an n-DOFs dynamical system, its mass, stiffness and damping matrices are denoted as M, K and C, respectively. The equation of motion in matrix format can be expressed as:

$$M\ddot{X}+C\dot{X}+KX=F \tag{3}$$

where X is the response variable vector and F is the load vector. According to structure dynamics, its N×N mode shape matrix, where N is the number of degrees of freedom, can be obtained from an FEM of the turbine blade by solving the eigensystem of $(M^{-1}K)$, at step 37. The resulting mode shape matrix $\Phi$ is expressed as EQ. (4)

$$\Phi = \begin{bmatrix} \phi_{1_1} & \cdots & \phi_{m_1} \\ \vdots & \ddots & \vdots \\ \phi_{1n} & \cdots & \phi_{mn} \end{bmatrix} \tag{4}$$

Each column of the matrix of EQ. (4) corresponds to one eigenvector and represents one mode shape. For example, the first column of the matrix is the 1st mode shape, the second column of the matrix is the 2nd mode shape, etc. The corresponding eigenvalues are related to the theoretical natural frequencies of the structure, represented using the mass matrix M and stiffness matrix K, under free vibration. The correlation is $f_i=\text{sqrt}(D_i)/(2\pi)$, where $D_i$ is the $i^{th}$ eigenvalue and $f_i$ is the $i^{th}$ natural frequency of the structure.

Based on the modal analysis, a transformation equation can be written as:

$$\frac{\phi_{ie}}{\phi_{iu}} = \frac{\delta_{ie}}{\delta_{iu}} \Rightarrow \delta_{iu} = \frac{\phi_{iu}}{\phi_{ie}}\delta_{ie} \tag{5}$$

where the subscript e represents DOFs, which can be measured by the sensor, u represents the DOFs that are inaccessible for measurements using sensors, and i represents the ith mode. $\varphi_{ie}$ represents the mode information for the eth DOF under the ith mode and $\delta_{ie}$ represents the modal response for the eth DOF under the ith mode. Recall that the measured response is filtered using the steps in FIG. 3, and the output of the filtering is an IMF. Thus, an IMF resulting from FIG. 3 is $\delta_{1e}$ in EQ. (5), where the subscript "i" in EQ. (5) is represent $i^{th}$ mode.

EQ. (5) builds a relationship between two coordinates in the structure. At step 38, using this equation, the modal response $\delta_{iu}$ at a sensor-inaccessible location can be computed from the modal response $\delta_{ie}$ at a measured location. The transformation equation is derived from finite element analysis of the structure and its simplicity ensures the computation is highly efficient Given the mode shape matrix $\Phi$ and the IMFs, the modal response at a desired location can readily be evaluated from EQ. (5). The modal superposition methodology can be applied to obtain the dynamic response in the time domain after all the modal responses have been calculated. Finally, the mode superposition is made to transfer the modal responses to physical responses.

As an example, suppose the measurement location is the 6th DOF (degree of freedom), and one would like to reconstruct the physical response at a location corresponding to the 2nd DOF. Therefore, subscript e=6 and subscript u=2. Assume matrix $\Phi$ is obtained by solving for the eigenvector of $(M^{-1}K)$. For first mode (i=1): process the measurement data using a method according to an embodiment of the disclosure as shown in FIG. 3. The result is an IMF, which is denoted $\delta_{16}$. Obtain the values of $\varphi_{16}$, $\varphi_{12}$ from the $\Phi$ matrix. Calculate $\delta_{12}$ from EQ. (5). For second mode (i=2): do the same thing as for the first mode, using $\varphi_{26}$, $\varphi_{22}$, and $\delta_{26}$ to obtain $\delta_{22}$. For third mode (i=3): do the same thing as for the first mode, using $\varphi_{36}$, $\varphi_{32}$, $\delta_{36}$ to obtain $\delta_{32}$. The above steps may be repeated until all significant modes are obtained. Recall that the significant modes are those that can be identified from the Fourier spectra of the measured data. Now the reconstructed response for the 2nd DOF is simply the summation of $\delta_{12}+\delta_{22}+\delta_{32}+\ldots$.

Once the stress and strain responses are reconstructed, a rainflow counting method can be used to obtain the rainflow matrix for the S-N curve-based fatigue life estimation. A da/dN-based approach can also be applied if there is a crack-like flaw.

A system and method according to embodiments of the disclosure has the following features as compared with a conventional system and method:

(1) A system and method according to embodiments of the disclosure needs a minimum of one measurement location to reconstruct the stress or strain fields of an entire blade.

(2) The stress and strain fields of the entire blade obtained by a method according to embodiments of the disclosure are the physical responses which can be directly related to other analyses, e.g., frequency domain analysis using Fourier spectra of the physical responses.

(3) The location of the measurement does not in theory affect the performance of a reconstruction method according to embodiments of the disclosure and no special optimization is needed to determine a best location for measurement.

Figure 8:
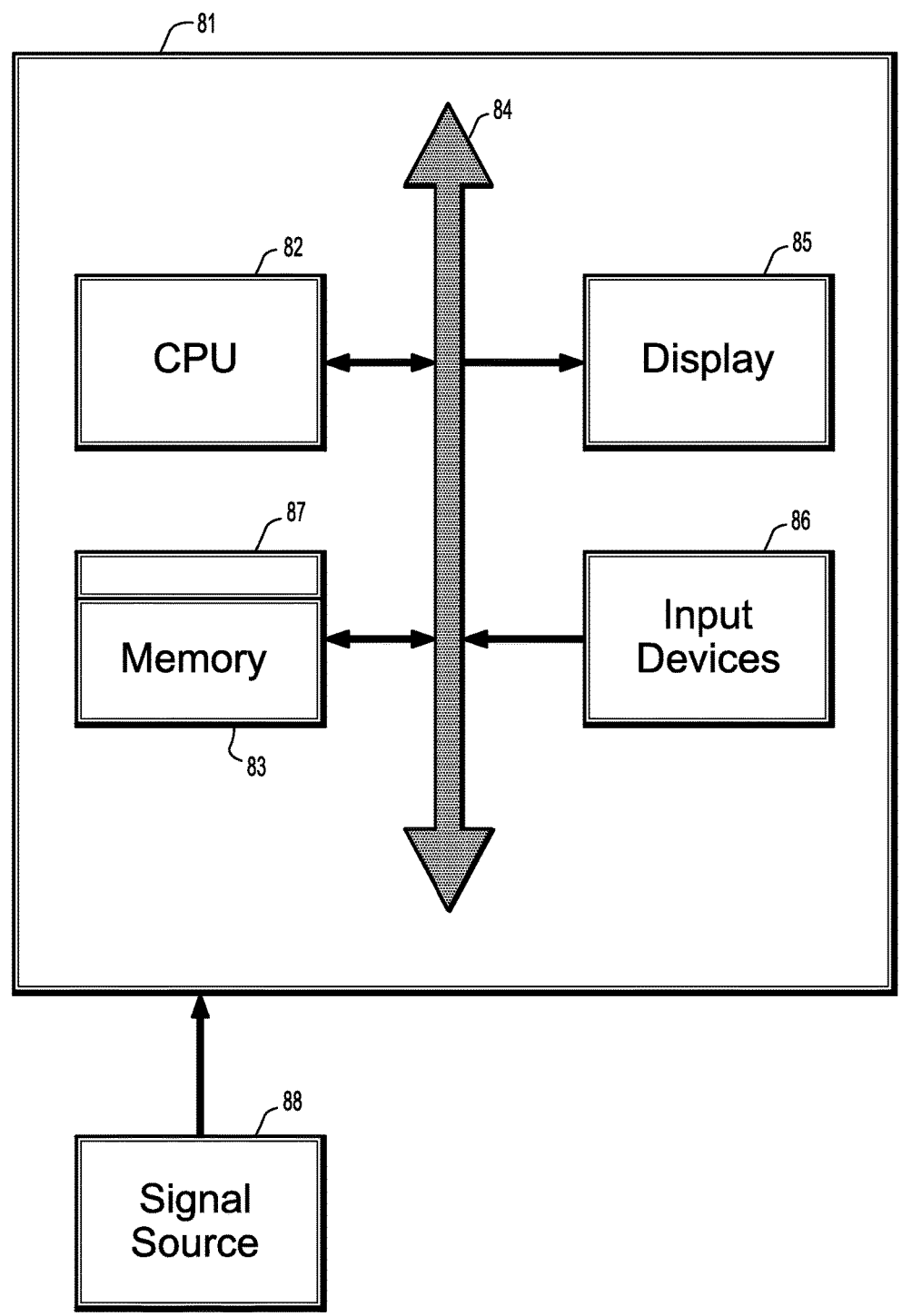
FIG. 8 is a block diagram of a system for dynamical response reconstruction, according to an embodiment of the disclosure.

(4) Because a system and method according to embodiments of the disclosure can reconstruct the stress and strain fields of an entire blade, an overview of the stress and strain distribution, the locations of hot spots and maximum stress, and other useful quantities can readily be obtained. A 3D visualization of the entire blade and the cross-section view of a given cutting plane can be conveniently implemented, as illustrated in FIG. 8.

(5) A system and method according to embodiments of the disclosure does not require additional hardware and modeling. The current input, such as a finite element model and the measurement data, can be directly used in a system and method according to embodiments of the disclosure. In addition, numerical simulations can be used with system and method according to embodiments of the disclosure to optimize the sensor layout. For example, based on a user-given or random loading profile, the hot spots where the stress and strain are much larger than other locations, or spots having large deflections, can be found by numerical simulation, and those locations can be reasonable candidates for measurement locations.

Figure 4:
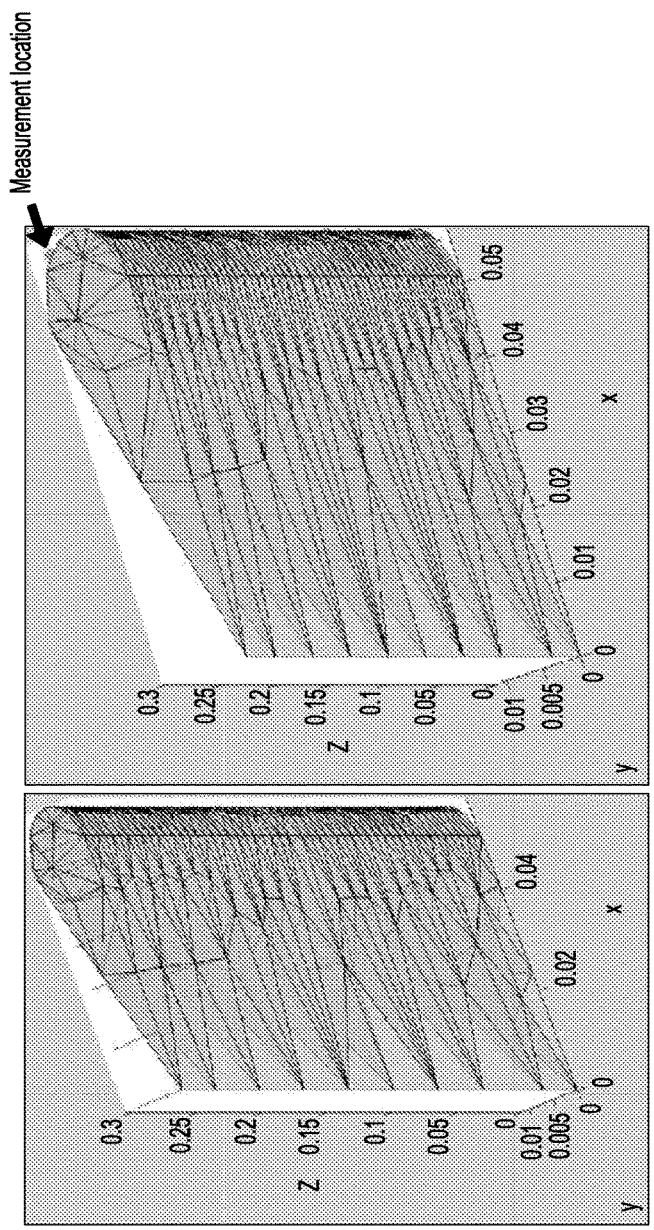
FIG. 4 depicts blade FEM model and measurement locations, according to an embodiment of the disclosure.
Figure 5:
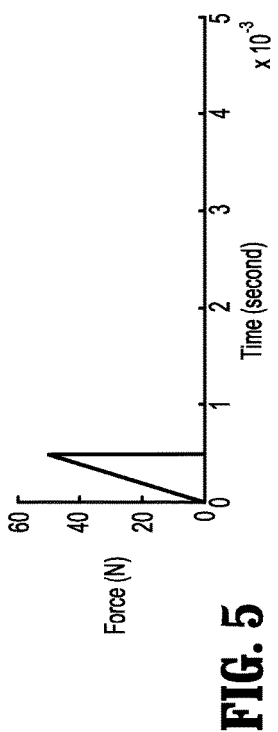
FIG. 5 depicts applied forces as a function of time, according to an embodiment of the disclosure.
Figure 6:
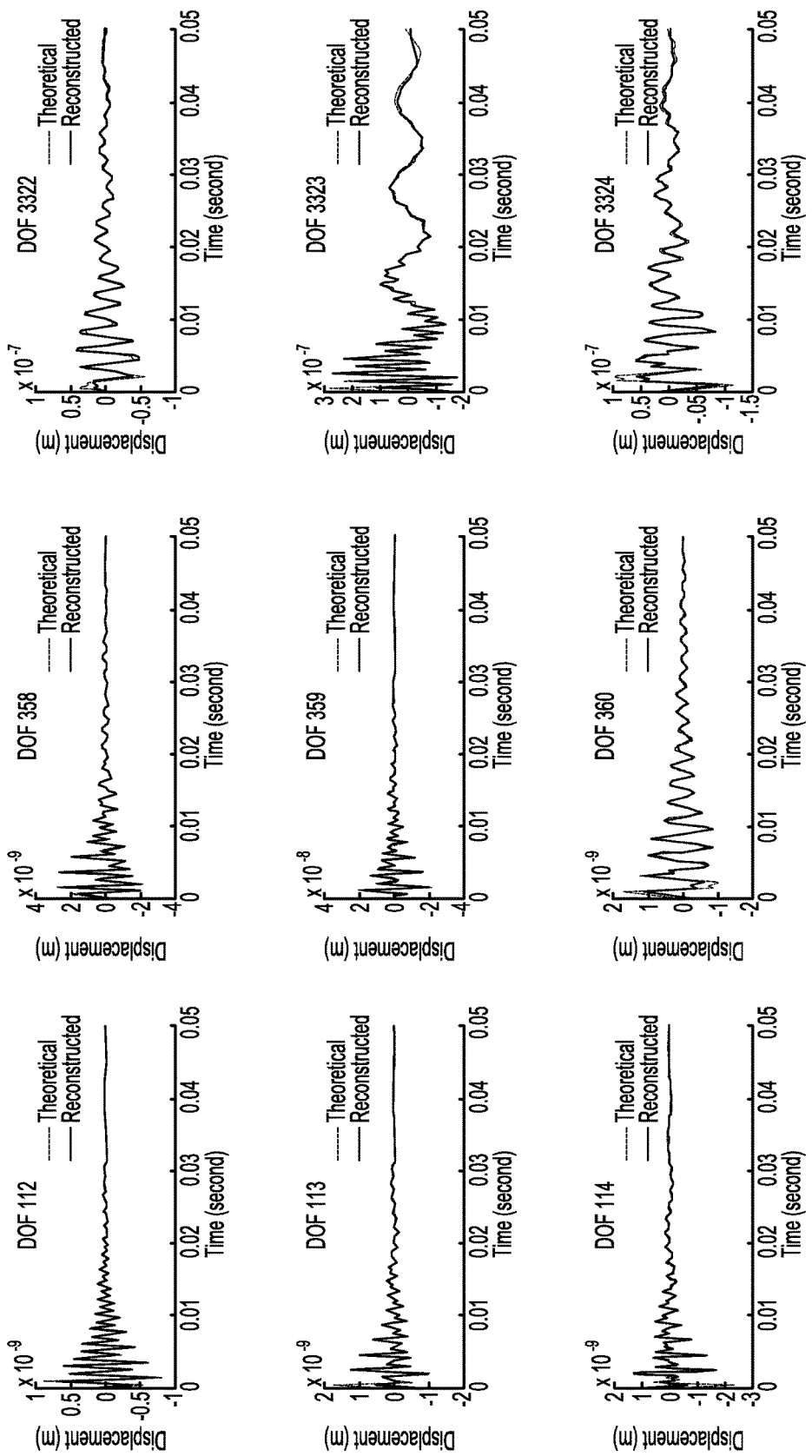
FIG. 6 shows graphs of comparisons between reconstructed results and theoretical solutions, according to an embodiment of the disclosure.

An illustrative example is given herein below to illustrate an overall idea according to embodiments of the disclosure. The example model is a blade subject to an impact load. Time domain responses are obtained by solving the equation of motion (EoM) of the finite element model. The response of an arbitrary location around the blade tip is chosen to represent the tip-timing measurement data. Using a method according to an embodiment of the disclosure, the dynamical responses of other locations of the blade are reconstructed using the representative measurement data. Results are compared with the direct solution of those locations using an FEM. FIG. 4 at (a) presents the blade FEM model and FIG. 4 at (b) depicts the tip-timing measurement location. All degree of freedoms (DOFs) are constrained for nodes on the x-y plane, i.e., nodes with z=0. The overall blade FEM model has 5820 active DOFs. The material of the blade is aluminum alloy. FIG. 5 is a graph of an applied force as a function of time. FIG. 6 depicts comparisons between the reconstructed deflection responses with the theoretical solution for selected degrees of freedom (DOF) using the measurement data with 10% noisy components. The reconstructed locations are arbitrarily chosen.

Figure 7:
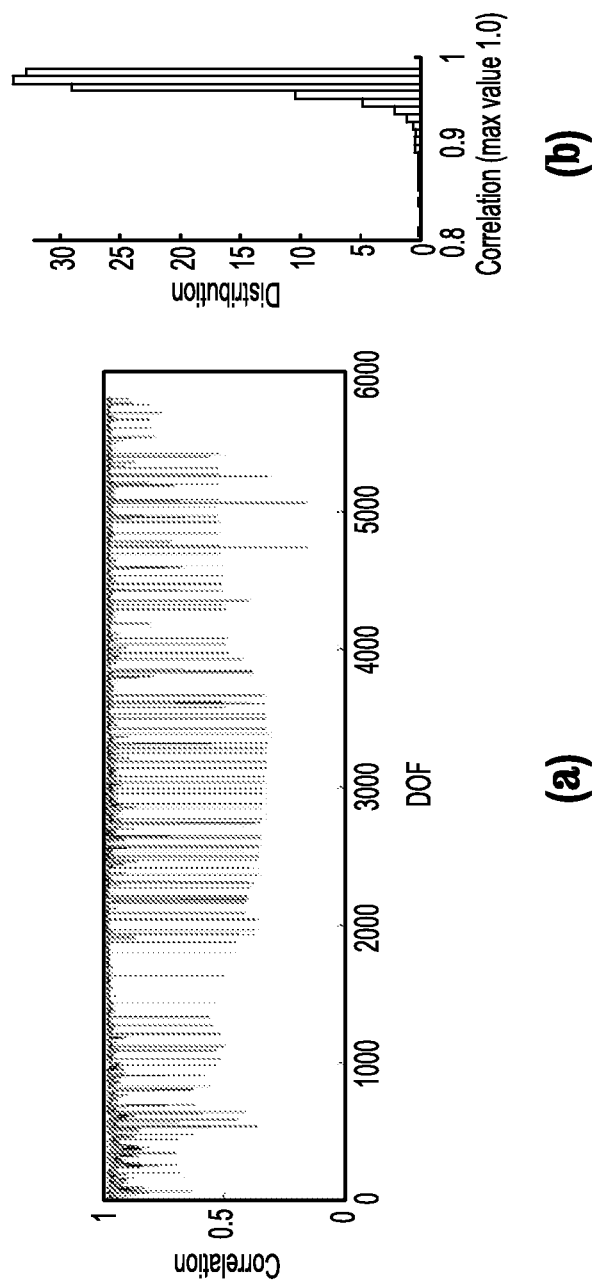
FIG. 7 illustrates a statistical performance as measured by the correction between reconstruction results and theoretical results, according to an embodiment of the disclosure.

The performance of a method according to embodiments of the disclosure can be quantified using the correlation coefficient of the reconstruction results with respect to the theoretical results. A perfect reconstruction result of a chosen location leads to a correlation coefficient of 1. Due to measurement noise and modeling uncertainty, the coefficient should be close to 1. FIG. 7 depicts the overall performance, using measurement data with 10% noisy components. FIG. 7 at (a) depicts correlation coefficients of all DOFs, and FIG. 7 at (b) depicts a normalized histogram of the coefficients. If a correlation coefficient larger than 0.9 is considered to be an accurate reconstruction, around 97% of all DOFs (total 5820 DOFs) can be accurately reconstructed in this example.

It is to be understood that embodiments of the present disclosure can be implemented in various forms of hardware, software, firmware, special purpose processes, or a combination thereof. In one embodiment, the present disclosure can be implemented in software as an application program tangible embodied on a computer readable program storage device. The application program can be uploaded to, and executed by, a machine comprising any suitable architecture.

FIG. 8 is a block diagram of a system for dynamical response reconstruction, according to an embodiment of the disclosure. Referring now to FIG. 8, a computer system 81 for implementing the present invention can comprise, inter alia, a central processing unit (CPU) 82, a memory 83 and an input/output (I/O) interface 84. The computer system 81 is generally coupled through the I/O interface 84 to a display 85 and various input devices 86 such as a mouse and a keyboard. The support circuits can include circuits such as cache, power supplies, clock circuits, and a communication bus. The memory 83 can include random access memory (RAM), read only memory (ROM), disk drive, tape drive, etc., or a combinations thereof. The present invention can be implemented as a routine 87 that is stored in memory 83 and executed by the CPU 82 to process the signal from the signal source 88. As such, the computer system 81 is a general purpose computer system that becomes a specific purpose computer system when executing the routine 87 of the present invention.

The computer system 81 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A method for dynamically reconstructing a stress and strain field of a turbine blade, comprising the steps of:
   receiving at a dynamic response reconstruction processor, a set of response measurements from at least one location on a turbine blade;

in the dynamic response reconstruction processor, bandpass filtering the set of response measurements based on an upper frequency limit and a lower frequency limit;

performing, in the dynamic response reconstruction processor, a fast Fourier transform to identify major frequency components of the response measurements to identify an upper envelope and a lower envelope of the set of response measurements from local minima and local maxima of the set of response measurements;

in the dynamic response reconstruction processor, calculating a candidate intrinsic mode function (IMF) by iteratively defining the upper and the lower envelope based on the local minima and maxima of the set of response measurements defining a mean envelope which is subtracted from time domain data in each iteration until a component of response measurements is an IMF;

providing an N×N mode shape matrix for each IMF associated with the turbine blade, wherein N is the number of degrees of freedom of the turbine blade; and in the dynamic response reconstruction processor, calculating a response for another location on the turbine blade from the IMF and mode shapes in the mode shape matrix by:

computing a modal response at a sensor-inaccessible location based on a second modal response at a measured location by multiplying the second modal response at the measured location times a ratio of a first modal information of the sensor-inaccessible location and a second modal information of the sensor accessible location derived from a finite element model for a given degree of freedom;

computing modal responses for a plurality of sensor-inaccessible locations for all mode shapes in the mode shape matrix to compute a dynamic response of an entirety of the turbine blade;

for each degree of freedom of the turbine blade, superimposing the modal responses for the sensor-inaccessible locations for each mode shape according to:

$$\delta_{superimposed} = \delta_{1d} + \delta_{2d} + \delta_{3d+\ldots} + \delta_{md};$$

where $\delta$ is a modal response for a given degree of freedom and mode;

d denotes the degree of freedom and m denotes the mode; and creating a three-dimensional visualization based on the superimposed computed modal responses of the turbine blade including a cross-sectional view of a given cutting plane.

2. The method of claim 1, wherein said upper frequency limit and said lower frequency limit of the set of response measurements are determined by Fourier transforming the set of response measurements and identifying major frequency components by peak picking.

3. The method of claim 1, wherein the at least one location on said turbine blade is a tip location.

4. The method of claim 1, wherein said upper envelope and said lower envelope of the set of response measurements are determined from cubic splines that connect the local minima and local maxima of the set of response measurements.

5. The method of claim 1, wherein calculating a candidate IMF from the upper envelope and the lower envelope of the set of response measurements comprises:

calculating a mean envelope of the upper envelope and the lower envelope of the set of response measurements; and calculating the candidate IMF by subtracting the mean envelope from the set of response measurements.

6. The method of claim 5, wherein if the candidate IMF is not an IMF, the steps of determining the upper envelope and the lower envelope and calculating a mean envelope of the upper envelope and the lower envelope are performed on the candidate IMF, and a new candidate IMF is calculated by subtracting the mean envelope of the previous candidate IMF from the previous candidate IMF.

7. The method of claim 1, further comprising repeating said steps of determining the upper envelope and the lower envelope of the set of response measurements and calculating a candidate IMF from the upper envelope and the lower envelope of the set of response measurements until no further IMFs can be calculated from the set of response measurements.

8. The method of claim 1, wherein the N×N mode shape matrix is calculated by solving the eigensystem of $(M^{-1}K)$, wherein M is a matrix that represents a mass of a turbine blade and K is a matrix that represents a stiffness of the turbine blade.

9. The method of claim 1, wherein calculating a response for another location on the turbine blade comprises calculating $$\delta_{iu} = \frac{\phi_{iu}}{\phi_{ie}} \delta_{ie},$$

wherein subscript e represents a degree of freedom (DOF) that can be measured, u represents a DOF that is inaccessible for measurements, and i represents an ith mode, $\varphi_{iu}$ -represents the mode shape for the uth DOF under the ith mode at the sensor inaccessible location, $\varphi_{ie}$ -represents the mode shape for the eth DOF under the ith mode at the sensor accessible location, and $\delta_{ie}$ represents the ith IMF for the eth DOF.

10. The method of claim 1, further comprising calculating an S-N curve-based fatigue life estimation from the calculated responses.

11. A method for dynamically reconstructing a stress and strain field of a turbine blade, comprising the steps of:

providing a set of response measurements from at least one location on a turbine blade to a dynamic response reconstruction processor;

in the dynamic response reconstruction processor, using empirical mode decomposition to determine intrinsic mode functions (IMFs) from a set of response measurements by iteratively defining an upper and a lower envelope based on the local minima and maxima of the set of response measurements defining a mean envelope which is subtracted from time domain data in each iteration until a component of response measurements is an IMF; and in the dynamic response reconstruction processor, calculating a response for another location on the turbine blade, wherein a mode shape is a component of an N×N mode shape matrix calculated by solving the eigenvectors of $(M^{-1}K)$, wherein M is a matrix that represents a mass of a turbine blade and K is a matrix that represents a stiffness of the turbine blade and computing modal responses for a plurality of sensor-inaccessible locations for all mode shapes in the mode shape matrix by multiplying a modal response for a first sensor-accessible location times a ratio of a first modal information of the sensor-inaccessible location and a second modal information of a sensor accessible location derived from a finite element model for a given degree of freedom to compute a dynamic response of an entirety of the turbine blade;

for each degree of freedom of the turbine blade, superimposing the modal responses for the sensor-inaccessible locations for each mode shape according to:

$$\delta_{superimposed} = \delta_{1d} + \delta_{2d} + \delta_{3d+\ldots} + \delta_{md};$$

where $\delta$ is a modal response for a given degree of freedom and mode;
d denotes the degree of freedom and m denotes the mode; and creating a three-dimensional visualization based on the computed modal responses of the turbine blade including a cross-sectional view of a given cutting plane.

12. The method of claim 11, wherein using empirical mode decomposition to determine IMFs comprises:
determining the upper envelope and the lower envelope of the set of response measurements from local minima and local maxima of the set of response measurements;
calculating a mean envelope of the upper envelope and the lower envelope of the set of response measurements; and
calculating the candidate IMF by subtracting the mean envelope from the set of response measurements.

13. The method of claim 11, further comprising,
determining an upper frequency limit and a lower frequency limit of the set of response measurements by Fourier transforming the set of response measurements and identifying major frequency components by peak picking; and
band-pass filtering the set of response measurements based on the upper frequency limit and the lower frequency limit, prior to using empirical mode decomposition to determine IMFs.

14. A non-transitory program storage device readable by a computer, tangibly embodying a program of instructions executed by the computer to perform the method steps for dynamically reconstructing a stress and strain field of a turbine blade, the method comprising the steps of:
providing a set of response measurements from at least one location on a turbine blade to a dynamic response reconstruction processor;
in the dynamic response reconstruction processor, band-pass filtering the set of response measurements based on an upper frequency limit and a lower frequency limit;
in the dynamic response reconstruction processor, determining an upper envelope and a lower envelope of the set of response measurements from local minima and local maxima of the set of response measurements;
in the dynamic response reconstruction processor, calculating a candidate intrinsic mode function (IMF) from the upper envelope and the lower envelope of the set of response measurements by iteratively defining an upper and a lower envelope based on the local minima and maxima of the set of response measurements defining a mean envelope which is subtracted from time domain data in each iteration until a component of response measurements is an IMF;
providing an N×N mode shape matrix for the turbine blade, wherein N is the number of degrees of freedom of the turbine blade when the candidate IMF is an IMF; and
in the dynamic response reconstruction processor, calculating a response for another location on the turbine blade from the IMF and mode shapes in the mode shape matrix by:
computing a modal response at a sensor-inaccessible location by multiplying a modal response for the sensor accessible location times a ratio of a first modal information of a sensor-inaccessible location and a second modal information of the sensor accessible location derived from a finite element model for a given degree of freedom;
computing modal responses for a plurality of sensor-inaccessible locations for all mode shapes in the mode shape matrix to compute a dynamic response of an entirety of the turbine blade;
for each degree of freedom of the turbine blade, superimposing the modal responses for the sensor-inaccessible locations for each mode shape according to:

$$\delta_{superimposed} = \delta_{1d} + \delta_{2d} + \delta_{3d+\ldots} + \delta_{md};$$

where $\delta$ is a modal response for a given degree of freedom and mode;
d denotes the degree of freedom and m denotes the mode; and creating a three-dimensional visualization based on the computed modal responses of the turbine blade including a cross-sectional view of a given cutting plane.

15. The computer readable program storage device of claim 14, wherein said upper frequency limit and said lower frequency limit of the set of response measurements are determined by Fourier transforming the set of response measurements and identifying major frequency components by peak picking.

16. The computer readable program storage device of claim 14, wherein the at least one location on said turbine blade is a tip location.

17. The computer readable program storage device of claim 14, wherein said upper envelope and said lower envelope of the set of response measurements are determined from cubic splines that connect the local minima and local maxima of the set of response measurements.

18. The computer readable program storage device of claim 14, wherein calculating a candidate IMF from the upper envelope and the lower envelope of the set of response measurements comprises:
calculating a mean envelope of the upper envelope and the lower envelope of the set of response measurements; and
calculating the candidate IMF by subtracting the mean envelope from the set of response measurements.

19. The computer readable program storage device of claim 18, wherein if the candidate IMF is not an IMF, the steps of determining the upper envelope and the lower envelope and calculating a mean envelope of the upper envelope and the lower envelope are performed on the candidate IMF, and a new candidate IMF is calculated by subtracting the mean envelope of the previous candidate IMF from the previous candidate IMF.

20. The computer readable program storage device of claim 14, the method further comprising repeating said steps of determining the upper envelope and the lower envelope of the set of response measurements and calculating a candidate intrinsic mode function (IMF) from the upper envelope and the lower envelope of the set of response measurements until no further IMFs can be calculated from the set of response measurements.

21. The computer readable program storage device of claim 14, wherein the N×N mode shape matrix is calculated by solving the eigensystem of $(M^{-1}K)$, wherein M is a matrix that represents a mass of a turbine blade and K is a matrix that represents a stiffness of the turbine blade.

22. The computer readable program storage device of claim 14, wherein calculating a response for another location on the turbine blade comprises calculating $$\delta_{iu} = \frac{\phi_{iu}}{\phi_{ie}} \delta_{ie},$$

wherein subscript e represents a degree of freedom (DOF) that can be measured, u represents a DOF that is inaccessible for measurements, and i represents an $i^{th}$ mode, $\varphi_{iu}$ represents the mode shape for the $u^{th}$ DOF under the $i^{th}$ mode at the sensor inaccessible location, $\delta_{ie}$ represents the mode shape for the $e^{th}$ DOF under the $i^{th}$ mode at the sensor accessible location, and $\sigma_{ie}$ represents the $i^{th}$ IMF for the $e^{th}$ DOF.

23. The computer readable program storage device of claim 14, further comprising calculating an S-N curve-based fatigue life estimation from the calculated responses.

\* \* \* \* \*